(12) United States Patent
Muz et al.

(10) Patent No.: US 9,989,548 B2
(45) Date of Patent: Jun. 5, 2018

(54) AUTOMATIC ANALYZER AND METHOD

(71) Applicant: Endress+Hauser Conducta GmbH+Co. KG, Gerlingen (DE)

(72) Inventors: Ulrike Muz, Stuttgart (DE); Annik Abel, Leonberg (DE); Justyna Homa, Gerlingen (DE); Thomas Schipolowski, Stuttgart (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 0 days. days.

(21) Appl. No.: 15/472,775

(22) Filed: Mar. 29, 2017

(65) Prior Publication Data

US 2017/0285054 A1 Oct. 5, 2017

(30) Foreign Application Priority Data

Mar. 30, 2016 (DE) .......................... 10 2016 105 770

(51) Int. Cl.
*G01N 35/10* (2006.01)
*G01N 35/00* (2006.01)

(52) U.S. Cl.
CPC .......... *G01N 35/1002* (2013.01); *G01N 35/00* (2013.01); *G01N 35/00623* (2013.01); *G01N 35/1016* (2013.01); *G01N 35/1065* (2013.01); *G01N 2035/00227* (2013.01);
(Continued)

(58) Field of Classification Search
CPC .......... G01N 2035/00227; G01N 2035/00306; G01N 2035/00465; G01N 2035/1025; G01N 35/00; G01N 35/00623; G01N 35/1002; G01N 35/1016; G01N 35/1065
See application file for complete search history.

(56) References Cited

U.S. PATENT DOCUMENTS 4,746,491 A * 5/1988 Ohlin ....................... G01N 1/38
137/625.42
5,731,211 A * 3/1998 Ohlin ....................... G01N 1/38
422/68.1

FOREIGN PATENT DOCUMENTS

CN 101650276 A 2/2010
DE 69524732 T2 11/2002
DE 10227032 A1 11/2003
(Continued)

OTHER PUBLICATIONS

Search Report for German Patent Application No. 10 2016 105 770.3, German Patent Office, dated Feb. 24, 2017, 8 pp.

*Primary Examiner* — Samuel P Siefke
(74) *Attorney, Agent, or Firm* — Christopher R. Powers; PatServe (57) ABSTRACT

The present disclosure relates to an automatic analyzer for determining a parameter of a sample fluid, including a dosing device comprising at least one dosing chamber, a first fluid flow path connecting a sample receiving vessel to the dosing chamber via a first pump, a tank containing a dilution medium, a second fluid flow path connecting the tank to the dosing chamber via a second pump, a measuring cell in communication with the dosing chamber via a third fluid flow path via a third pump, and a measuring and control system connected to and configured to control the pumps, wherein the first, second, and third fluid flow paths can selectively be blocked or unblocked by at least one valve unit and the measuring and control system is configured to control the at least one valve unit to block or unblock the first, second, and third flow paths.

18 Claims, 1 Drawing Sheet

(52) U.S. Cl.
 CPC .............. *G01N 2035/00306* (2013.01); *G01N 2035/00465* (2013.01); *G01N 2035/1025* (2013.01)

(56) References Cited

FOREIGN PATENT DOCUMENTS

DE           10222822  A1     12/2003
DE        102009029305 A1      3/2011

* cited by examiner

AUTOMATIC ANALYZER AND METHOD

CROSS-REFERENCE TO RELATED APPLICATION

The present application is related to and claims the priority benefit of German Patent Application No. 10 2016 105 770.3, filed on Mar. 30, 2016, the entire contents of which are incorporated herein by reference.

TECHNICAL FIELD

The present disclosure relates to an automatic analyzer for determining a parameter of a sample fluid, in particular a liquid sample, and a method for operating an analyzer.

BACKGROUND

In process measuring technology, e.g., in chemical, biotechnological, pharmaceutical, and food technology processes, as well as in environmental metrology, automatic analyzers are used to determine a measurand in a liquid sample. Analyzers may, for example, be used for the monitoring and optimization of the cleaning performance of a sewage treatment plant, monitoring drinking water, or monitoring quality of foods. Measured and monitored is, for example, the proportion of a certain substance, which is also called an analyte, in a sample fluid, such as a liquid or a liquid mixture, an emulsion, a suspension, a gas, or a gas mixture. Analytes may, for example, be ions, such as ammonium, phosphate, silicate or nitrate, calcium, sodium or chloride, or biological or biochemical compounds, e.g., hormones, or even micro-organisms. Other parameters that are determined using analyzers in process measuring technology, including in the field of water control, are sum parameters, such as total organic carbon (TOC), total nitrogen (TN), total phosphorus (TP), or chemical oxygen demand (COD). Analyzers may, for example, be designed as cabinet devices or buoys.

The sample to be analyzed is often treated in analyzers by mixing it with one or more reagents, thus causing a chemical reaction in the reaction mixture. The reagents are preferably selected such that the chemical reaction is verifiable by physical methods, e.g., by optical measurements, using potentiometric or amperometric sensors, or through a conductivity measurement. Using a sensing element, measured values of a measurand correlated with the analysis parameter (e.g., COD) actually to be determined are detected accordingly. The chemical reaction may, for example, cause a coloring or a change of color that can be detected using optical means. In this case, the intensity of the color is a measure of the parameter to be determined. As a measurand correlated with the parameter to be determined, an absorption or extinction of the sample treated may, for example, be determined by photometric means by feeding electromagnetic radiation, such as visible light, from a radiation source into the liquid sample, and receiving it with a suitable receiver after transmission through the liquid sample. The receiver generates a measurement signal, which depends upon the intensity of the radiation received and from which the value of the parameter to be determined can be derived for example, based upon a calibration function or a calibration table.

In order to use such methods of analysis in an automated manner, e.g., in the industrial sector or for monitoring a sewage treatment plant or a body of water outdoors, it is desirable to provide an analyzer that executes the required analytical processes in an automated manner. In addition to a sufficient measurement accuracy, the most important requirements for such an analyzer are robustness, easy operability, and the guarantee of sufficient occupational and environmental safety.

Automatic analyzers are already known from the prior art. For example, DE 102 22 822 A1, DE 102 27 032 A1, and DE 10 2009 029305 A1 show online analyzers for analyzing measuring samples. These online analyzers are respectively designed as a cabinet device, having an electronic measuring and control system, supply tanks for reagents, standard solutions and cleaning liquids, pumps for delivering and dosing the liquid sample and the reagent or reagents into a measuring cell, and a sensing element for optical measurements on the liquid sample contained in the measuring cell and converted using the reagent or reagents. The reagents, standard solutions, or cleaning liquids are taken from the supply tanks and transported into the measuring cell. Accordingly, spent liquid is transferred from the measuring cell into a waste tank.

In certain applications, it may be required to dilute the sample fluid prior to supplying it to the measuring cell for example, in order to cover a broader concentration range of the analyte. From CN 101 650 276 A is known an automatic analyzer for determining a sugar concentration in a fermentation process, in which the samples taken from the fermenter are diluted with water. This takes place by means of two pumps, the feed rates of which are determined and set by a control computer in order to set a dilution ratio.

However, this setting of the dilution ratio, i.e., the dosing of the sample fluid and of a dilution medium to be mixed with the sample fluid, by controlling two separate pumps has disadvantages: The transport of the fluids in automatic analyzers takes place via fluid lines, the respective internal volume of which can change over the service life of the devices for example, by gradual clogging of the fluid lines with a polluting load present in the sample fluid or by other formation of deposits or vegetation inside the fluid lines. If the fluid lines are made of a polymer material, their internal volume can also change as a result of aging of the polymer material for example, as a result of hardening or flowing of the polymer material. The pumps used can also be exposed to aging and material fatigue, so that the fluid volume transported using a pump with given operating parameters and given transport time also called the feed rate changes over the service life of the pump. Such signs of aging become particularly highly noticeable in the hose lines and hose pumps often used in automatic analyzers. Hose pumps also called peristaltic pumps transport the fluid to be delivered by means of external mechanical deformation of the hose lines. As a result of the mechanical loading of the hose lines, a significant change in the fluid volume delivered with given pump parameters occurs within relatively short periods of time. If the dosing of the sample fluid and the dilution medium is thus carried out solely by controlling the pumps, the actual feed rate, and thus the actually delivered fluid volume over the service life of the analyzer, changes with aging of the pumps or of the hose lines. Since it cannot be assumed that the aging of both pumps or of the respective fluid lines takes place to the same extent, the actually available dilution ratio thus also changes. This can basically be compensated for by a routine adjustment in combination with an early exchange of the fluid lines and/or the pumps. The routine performance of these measures is, however, labor-intensive and causes routine interruptions of the operation of the analyzer.

BRIEF SUMMARY

It is, therefore, the aim of the present disclosure to specify an improved generic analyzer and a method for operating the analyzer. In particular, the analyzer is to be designed such that a stable dilution ratio can be set for the long term, without frequent maintenance measures being required.

This aim is achieved by the analyzer according to claim 1 and the method according to claim 15. Advantageous embodiments are listed in the dependent claims.

The automatic analyzer according to the present disclosure for determining a parameter of a sample fluid in particular, a sample liquid comprises: a dosing device comprising at least one dosing chamber; a first fluid flow path, which fluidically connects a sample receiving vessel to the dosing chamber; a first pump, which is integrated into the first fluid flow path for the fluid transport along the first fluid flow path; a tank containing a dilution medium; a second fluid flow path, which fluidically connects the tank containing the dilution medium to the dosing chamber; a second pump, which is integrated into the second fluid flow path for the fluid transport along the second fluid flow path; a measuring cell, which encloses a cavity, that communicates with the dosing chamber via a third fluid flow path; a third pump, which is connected to the dosing chamber; and an electronic measuring and control system, which is connected to the first, second, and third pumps and which is designed to control the pumps; wherein the first, second, and third fluid flow paths can respectively selectively be blocked or unblocked by means of at least one valve unit and wherein the electronic measuring and control system is additionally designed to control the at least one valve unit in order to block or unblock the first, second, and third flow paths.

By the sample receiving vessel and the tank containing the dilution medium always being in fluid communication with the dosing chamber, and the dosing chamber in turn being in fluid communication with the measuring cell, it is possible to carry out the dosing of the sample fluid and the dilution medium, which are mixed together and supplied to the measuring cell, by means of the dosing device. As a result, it is irrelevant whether or not the fluid volume actually delivered by the first and the second pumps per time unit changes over the service life of the pumps. In this way, a stable dilution ratio can be set for the long term.

The dosing device can provide a certain dosing volume for example, as a result of the measurements of the dosing chamber, or by means of fill level detectors, e.g., light barriers, arranged in or on the dosing chamber.

The sample receiving vessel can be a tank that is a component of the analyzer. Alternatively, the sample receiving vessel can be a tank that is spatially separated from the analyzer, but fluidically connected to the dosing chamber.

A valve unit in this case refers to a functional part that is able to selectively block or unblock a fluid transport along a fluid flow path. This may be a traditional valve, such as a constriction-hose valve. It is, however, also possible that a pump in particular, the first, the second, and/or the third pump have a valve function, in that it either transports fluid along a fluid flow path in an active operating state (fluid flow path unblocked) or blocks the transport of a fluid in an inactive operating state, in which it does not transport any fluid along the fluid flow path. Peristaltic pumps generally have such a valve function and can therefore serve as a valve unit within the meaning of this present disclosure.

The at least one valve unit, by means of which the first, second, and third fluid flow paths can be selectively blocked or unblocked, can be a single, multi-way valve or an arrangement consisting of several individual valves, or of individual valves and at least one pump with a valve function.

The automatic analyzer can further comprise a mixing tank communicating with the dosing chamber via a fourth fluid flow path, wherein the fourth flow path can be selectively blocked or unblocked by means of a valve unit controlled by the measuring and control device. The valve unit can differ from the aforementioned at least one valve unit, by means of which the first, second, and third fluid flow paths can respectively be blocked or unblocked.

The dosing device can have at least one detector, comprising, in particular, at least one light barrier, which detector is designed to generate an electrical signal if a specified fill level in the dosing chamber is exceeded or fallen below and to output it to the electronic measuring and control system, wherein the electronic measuring and control system is designed to receive and process the electrical signal output by the detector and to control the first, second, or third pump based upon the electrical signal output by the detector, in order to dose specified volumes of fluids contained in the dosing chamber.

The first fluid flow path can be constituted by a first fluid line in particular, a hose which fluid line opens into the sample receiving vessel on one end and the other end of which is fluidically connected to the dosing chamber.

The analyzer can further comprise a second fluid line in particular, designed as a hose which fluid line opens on one end into the tank containing the dilution medium, the other end of which is fluidically connected to the dosing chamber so that the second fluid flow path runs through the second fluid line.

The first and the second pumps can, as mentioned, be operable in different operating modes. The first pump integrated into the first fluid flow path can be designed to transport fluid along the first fluid flow path in a first operating mode, and to block the first fluid flow path in a second operating mode, and the second pump integrated into the second fluid flow path can be designed to transport fluid along the second fluid flow path in a first operating mode, and to block the second fluid flow path in a second operating mode.

The analyzer can further comprise a third fluid line in particular, designed as a hose which fluid line opens into the measuring cell on one end and the other end of which is fluidically connected to the dosing chamber so that the third fluid flow path runs through the third fluid line, and wherein the third fluid line can be selectively blocked or unblocked by means of a first valve controlled by the electronic measuring and control system.

The analyzer can further comprise a fourth fluid line in particular, designed as a hose which fluid line opens into the mixing tank on one end and the other end of which is fluidically connected to the dosing chamber so that the fourth fluid flow path runs through the fourth fluid line, wherein the fourth fluid line can be selectively blocked or unblocked by means of a second valve controlled by the electronic measuring and control system.

The first and the second pumps can be respectively designed as peristaltic pumps. The third pump can be designed as a piston pump, which comprises a cylinder communicating with the dosing chamber and a movable piston, sealing off the cylinder in a fluid-tight manner from the environment, within the cylinder. The peristaltic pumps have the advantage that they can transport relatively large fluid volumes in a short period of time, while the piston pump is more suitable for precise dosing and is only subject to aging to a small extent.

The dosing chamber and/or the third pump communicate in an embodiment with a gas supply line, via which the third pump can take in gas in particular, air from the environment. The gas can advantageously be transported via the already mentioned fourth fluid flow path into the mixing tank in order to mix the fluid mixture present in the mixing tank and to possibly stir up any solid particles contained therein. This can, in particular, take place shortly before supplying the sample fluid-dilution medium mixture from the mixing tank to the dosing chamber and subsequent further transport of a dosed quantity of the fluid mixture as sample into the measuring cell via the third fluid flow path in order to achieve a good mixing of the sample.

In an embodiment, a first overflow line, which can, for example, be designed as a hose, opens into an upper region of the dosing chamber. Advantageously, the aforementioned gas supply line can serve as overflow line at the same time. The other end of the overflow line is arranged in the vicinity of a leak detector, such that the leak detector detects fluid escaping from this end of the overflow line. In an embodiment of the analyzer, a second overflow line opens into an upper region of the mixing tank, which overflow line runs to the same leak detector as the first overflow line, or to a second leak detector. In addition, a third overflow line can open into an upper region of the measuring cell, which overflow line runs to the same leak detector as the first and/or second overflow line, or to a third leak detector. The leak detector or the possibly provided several leak detectors are designed to generate an electrical signal when in contact with fluid escaping from the overflow lines and to output it to the electronic measuring and control system. For this purpose, they are connected to the electronic measuring and control system.

The dosing chamber can be fluidically connected via a valve unit which can be controlled by the electronic measuring and control system and which comprises a plurality of valves to a plurality of tanks, in which are contained different fluids in particular, one or more reagents, one or more calibration standards, one or more cleaning fluids, and fluids spent by the analyzer. By unblocking fluid flow paths running from the tanks into the dosing chamber by means of the valve unit in particular, by means of the third pump fluids can be delivered from the tanks into the dosing chamber, and a specified quantity, set by the dosing device, of the fluids respectively delivered into the dosing chamber can be transported further into the measuring cell. This process can be controlled and performed in accordance with a specified sequence by the electronic measuring and control system.

In order to determine values of the parameter to be monitored, the analyzer can comprise a sensing element, which is arranged in or on the measuring cell in order to detect a measurand, correlated with the parameter of the fluid sample, of a fluid or fluid mixture contained in the cavity of the measuring cell, and which is designed to generate an electrical measurement signal dependent upon the measurand and to output it to the electronic measuring and control system, wherein the electronic measuring and control system is designed to process the measurement signal generated by the sensing element in particular, to determine a value of the parameter based upon the measurement signal. The sensing element can, for example, be designed as a photometric or spectro-photometric sensing element. In this case, the measuring cell advantageously comprises a housing, the wall of which is transparent to the measuring radiation of the photometric or spectro-photometric sensing element for example, by the wall completely consisting of a material transparent to the measuring radiation, or by the wall at least having windows made of such a material. In this embodiment, the sensing element comprises at least one radiation source, which emits measuring radiation and which can, for example, comprise at least one LED, as well as at least one photoelectric detector. The photoelectric detector is arranged with respect to the radiation source such that the measuring radiation emitted by the radiation source passes through the measuring cell and a fluid possibly contained in the cavity enclosed by the measuring cell. The detector is designed to generate an electrical measurement signal dependent upon the intensity of the measuring radiation received, which measurement signal is a measure of the measurand, e.g., an absorption or extinction, correlated with the parameter to be determined. The electronic measuring and control system can be designed to control the sensing element in particular, the radiation source.

The present disclosure also comprises a method for operating an automatic analyzer in particular, an analyzer according to one of the embodiments described above. The method comprises the following steps: transporting a sample fluid from a sample receiving vessel into a dosing chamber of a dosing device of the analyzer by means of a first pump; dosing a specified volume of the fluid by means of the dosing device; transporting dilution medium from the tank containing the dilution medium into the dosing chamber by means of a second pump; dosing a specified volume of the dilution medium by means of the dosing device; and mixing the specified volume of the sample fluid with the specified volume of the dilution medium.

As already stated above, a precise mixing ratio that is stable for the long term results by using the dosing device for dosing the volumes to be mixed, compared to dosing solely by means of the control of the first and second pumps.

The mixing of the specified volume of the sample fluid with the specified volume of the dilution medium can comprise the following steps: transporting the specified volume of the sample fluid into a mixing tank by means of a third pump communicating with the dosing chamber; transporting the specified volume of the dilution medium into the mixing tank by means of a third pump.

The method for operating the automatic analyzer can further comprise: transporting a gas or gas mixture into and/or through a mixture formed in the mixing tank by mixing the specified volume of the sample fluid with the specified volume of the dilution medium; transporting at least a part of the mixture into the dosing chamber by means of the third pump; dosing a specified volume of the mixture by means of the dosing device; transporting the specified volume of the mixture into a measuring cell; transporting at least one reagent into the measuring cell; detecting a measured value of a measurand, correlated with a parameter to be determined of the sample fluid, of the mixture present in the measuring cell and mixed with the reagent; and determining a value of the parameter based upon the detected measured value.

Advantageously, all method steps can be performed in an automated manner by means of an electronic measuring and control system. The electronic measuring and control system can, in particular, comprise at least one data storage unit and at least one processor and/or microprocessor. In the data storage unit and/or a storage unit of the microprocessor, a computer program can be stored, which the processor or the microprocessor can run to control the analyzer in order to carry out the method steps described.

BRIEF DESCRIPTION OF THE DRAWINGS

In the following, the present disclosure is described in more detail with reference to the exemplary embodiment shown in the FIGURE, which shows.

DETAILED DESCRIPTION

Figure 1:
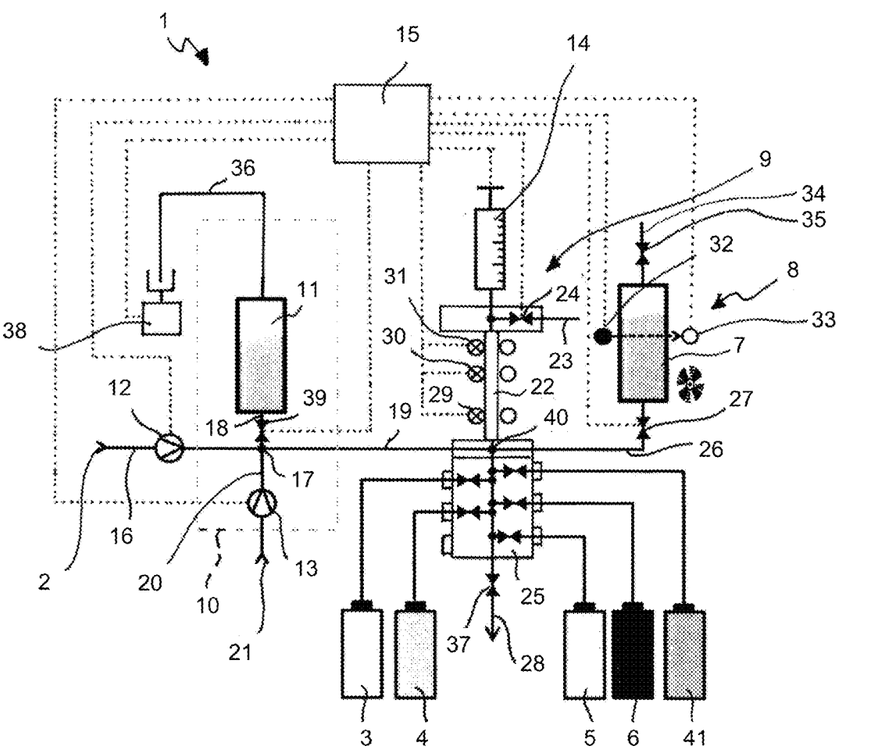
FIG. 1 shows a schematic representation of an automatic analyzer according to the present disclosure.

The analyzer 1 shown schematically in FIG. 1 is used to determine a parameter dependent upon at least one concentration of an analyte in a sample liquid serving as sample fluid. The analyzer 1 can, for example, be designed as a cabinet device, in which all components shown in FIG. 1 are combined in a cabinet (not shown). The parameter can, for example, be a sum parameter, such as chemical oxygen demand (COD) or total phosphorus (TP). The parameter can also be the concentration of a single substance, e.g., of a single ion type, such as sodium, ammonium, nitrate, or chloride. The sample fluid to be monitored by means of the analyzer 1 is provided in a sample receiving vessel 2. The sample fluid can, in particular, be a liquid, a liquid mixture, a multiphase mixture, e.g., a suspension or an emulsion in particular, a liquid with a solid load. The sample receiving vessel 2 can, for example, be a tank connected to a sampling point of a process to be monitored, into which tank the sample fluid is transported from the sampling point by means of a pump (not shown). The sample receiving vessel 2 can be part of the cabinet device or can be arranged remotely from it.

The analyzer 1 has several tanks 3, 4, 5, 6 and 41, which contain the reagents to be added to the sample fluid in order to determine the parameter, standard solutions for calibrating and/or adjusting the analyzer 1, and/or cleaning liquid. The analyzer 1 further comprises a measuring cell 7, a photometric sensing element 8, a dosing device 9 and a dilution module 10 with a mixing tank 11. In addition, the analyzer 1 comprises a plurality of fluid lines, which are designed in the present example as hose lines made of a flexible plastic material. The hose diameter is advantageously in the millimeter range, e.g., 1.6 mm, so that only small quantities of the sample fluid and other reagents are respectively needed for one analysis cycle, i.e., for the determination of a single value of the parameter. Another advantage of such a small hose diameter also consists in the blocking of a fluid line at a point, such as at an end of the line, stopping the transport of fluid over its entire length. As a result, the analyzer 1 of the present example has only a relatively small number of valves. In order to transport fluids through the fluid lines, the analyzer 1 comprises a first pump 12, a second pump 13, and a third pump 14. In order to control the automated analyzer 1 and to determine values of the parameter to be determined, the analyzer 1 has an electronic measuring and control system 15.

A first fluid line 16, which is connected at a crossing point 17 to a second fluid line 18, a third fluid line 19, and a fourth fluid line 20, opens into the sample receiving vessel 2. The first pump 12 arranged in the first fluid line 16 is, in the present example, designed as a hose pump and acts upon the fluid line 16 from outside, deforming it, in order to transport the sample fluid from the sample receiving vessel through the fluid line 16. The pump 12 can be operated in two operating modes: in the first ("active") operating mode, the pump 12 causes a fluid transport through the fluid line 16, whereas, in the second ("inactive") operating mode, it blocks a fluid transport through the fluid line 16 and thus functions as a valve unit. The pump 12 is connected to the electronic measuring and control system 15 so that the control system 15 can control the pump 12 in accordance with a specified sequence program. Of course, a pump which does not have a valve function, i.e., cannot block the fluid line 16 for a fluid transport, can, alternatively, also be used. In this case, an additional valve, which assumes this function, is arranged in the fluid line.

The second fluid line 18 connects the crossing point 17 to the mixing tank 11. In the second fluid line 18 is arranged an electrically actuatable valve 39, which can selectively block or unblock the fluid transport through the fluid line 18. The electronic measuring and control system 15 is connected to the valve 39 in order to control the blocking or unblocking of the fluid line 18 by actuating the valve 39. The third fluid line 19 connects the crossing point 17 to the dosing device 9.

The fourth fluid line 20 connects the crossing point 17 to a supply line 21 for a dilution medium, such as a dilution fluid, which, in the present example, is pure water. This can, for example, be provided in a tank (not shown in FIG. 1). In the present example, the second pump 13 is designed, like the first pump 12, as a hose pump that can be controlled by the electronic measuring and control system 15. It, too, can be operated in two operating modes like the first pump 12, wherein it transports fluid through the fluid line 20 in the first operating mode, whereas, in the second operating mode, it blocks a fluid transport through this line.

The dosing device 9 comprises a dosing vessel, which is in this case designed as a glass tube and which encloses a dosing chamber 22, in this case, the lumen of the glass tube. The third pump 14 communicates with the dosing chamber 22, which pump 14 is designed in the present example as a piston pump, which comprises a cylinder communicating with the dosing chamber 22 and a movable piston, sealing the cylinder on the rear side in a fluid-tight manner, within the cylinder. The pump 14 can be operated by means of a linear motor, which is controlled by the electronic measuring and control system 15. The pump 14 is connected to the dosing vessel 22 via a fluid line, into which opens a gas supply line 23 that can be selectively blocked or unblocked by a valve 24 controllable by the electronic measuring and control system 15. Via the gas supply line 23, the third pump 14 can draw in air from the environment. In the same way, the gas supply line 23 can serve as a pressure compensating line for the dosing chamber 22 and as an overflow line. The gas supply line 23 runs to a leak detector 38 (route not shown in FIG. 1 for the sake of clarity) so that its other end is arranged in the vicinity of the leak detector 38, such that the latter can detect fluid escaping from the gas supply line 23. The leak detector 38 is used to detect the overflowing of the mixing tank 11. It can, for example, be designed as a capacitive leak sensor. The leak detector 38 can optionally be connected to the electronic measuring and control system 15 and can be designed to send a signal to the electronic measuring and control system 15 if said leak detector 38 detects fluid escaping from the gas supply line 23. Based upon this signal, the electronic measuring and control system 15 can output a warning or alarm signal.

The third fluid line 19 is connected via another crossing point 40 to a supply line opening into the dosing chamber 22. The crossing point 40 also connects the dosing chamber 22 and the third fluid line 19 via a central valve unit 25 to the tanks 3, 4, 5, 6, and 41 as well as to a discharge line 28 for spent fluids, which discharge line 28 can be selectively blocked or unblocked by means of a valve 37. The electrically actuatable valve 37 is connected to the electronic measuring and control system 15 (route not drawn in FIG. 1 for the sake of clarity), which can control the blocking and unblocking of the discharge line 28. The crossing point 40, furthermore, connects the dosing chamber 22 and the third fluid line 19 to a fifth fluid line 26, which opens into the measuring cell 7. In addition, a pressure compensating line 34, which can be closed by means of a valve 35, opens into the measuring cell 7. This valve 35 can also be actuated by the electronic measuring and control system 15 (route not drawn in FIG. 1 for the sake of clarity), which can control the blocking and unblocking of the pressure compensating line 34. The pressure compensating line 34 also serves as overflow line to the leak detector 38. In the fifth fluid line 26 is arranged an electrically actuatable valve 27, which selectively unblocks or stops the fluid transport through the fluid line 26. The electronic measuring and control system 15 is connected to the valve 27 in order to control the valve 27.

The central valve unit 25 comprises a plurality of valves, which selectively allow or block the transport of fluids in particular, of liquids such as reagents or cleaning liquids from the tanks 3, 4, 5, 6 and 41 or the transport of fluids from the dosing chamber 22 into the discharge line 28. The valve unit 25 is connected to the electronic measuring and control system 15, which is designed to actuate the valves of the valve unit 25 in order to transport fluids, in particular, liquids from the tanks 3, 4, 5, 6 and 41 or to discharge spent fluids from the mixing tank 11 or the measuring cell 7 via the dosing chamber 22 in accordance with a specified sequence program.

Along the wall of the housing surrounding the dosing chamber 22, in this case, the already mentioned glass tube, several detectors 29, 30, 31 are arranged at different heights of the housing. The detectors 29, 30, 31 are designed to each generate an electrical signal and to output it to the electronic measuring and control system 15 when a fluid contained in the dosing chamber 22 exceeds a fill level specified by the position of the respective detector. The detectors 29, 30, 31 are designed as light barriers in the present example. Based upon the electrical detector signals, the electronic measuring and control system 15 can control the first, second, and/or third pump 12, 13, 14 in order to dose a certain fluid quantity by setting a certain fill level in the dosing chamber 22.

The photometric sensing element 8 comprises a radiation source 32, which is designed to emit measuring radiation of one or more specified wavelengths, and a radiation detector 33, which is designed to receive the measuring radiation and to generate an electrical measurement signal dependent upon the intensity of the measuring radiation received. The wavelength or the wavelengths of the measuring radiation are adapted to the parameter to be determined or to the verification method used to determine the parameter, so that the extinction or absorption of the measuring radiation used in a reaction mixture formed during the verification method is a measure of the value of the parameter in the sample fluid. The radiation source 32 can, for example, comprise one or more light-emitting diode. The radiation detector 33 can comprise one or more photoelectric elements, such as one or more photodiodes. In the present example, the wall of the measuring cell 7 is made from a material transparent to the measuring radiation, such as glass, in the case the measuring radiation is visible light. The radiation source 32 and the radiation detector 33 are arranged on opposite sides of the measuring cell 7 so that measuring radiation emitted by the radiation source 32 along an optical path running through the measuring cell 7 strikes the detector 33. The light intensity striking the detector 33 thus depends upon the extinction or absorption of a fluid or fluid mixture contained in the measuring cell 7. A sensor circuit (not explicitly shown) possibly amplifies and/or digitizes the electrical signal of the detector. The electronic measuring and control system 15 is designed, on the one hand, to control the radiation source 32 in order to emit measuring radiation. On the other hand, the electronic measuring and control system 15 is designed to receive and further process the signals of the detector 33. The further processing comprises, in particular, the determination of values of the parameter to be determined, based upon the signals of the detector 33.

An overflow line 36, which runs to the leak detector 38, opens in an upper region into the mixing tank 11, so that an overflowing of the mixing tank 11 can be detected by means of the leak detector 38.

The analyzer 1 shown in FIG. 1 is designed to dilute a sample fluid taken from the sample receiving vessel 2 in an automated manner using the dosing device 9 and the mixing tank 11 and to ascertain the parameter to be determined based upon a sample of the diluted sample fluid. This is described in detail below.

A first fluid flow path, which includes the fluid lines 16, 19 and the crossing points 17 and 40, runs between the sample receiving vessel 2 and the dosing chamber 22. A second fluid flow path, which includes the fluid line 20, the crossing point 17, the line 19, the crossing point 40, and the supply line opening into the dosing chamber 22, runs between the dosing chamber 22 and the supply line 21 for the dilution fluid. A third fluid flow path runs between the dosing chamber 22 and the measuring cell 7, viz, through the supply line opening into the dosing chamber 22, the crossing point 40, and the fluid line 26. A fourth fluid flow path runs between the dosing chamber 22 and the cavity enclosed by the mixing tank 11. The fourth fluid flow path includes the supply line opening into the dosing chamber 22, the crossing point 40, the fluid line 19, the crossing point 17 and the fluid line 18.

In order to mix a specified volume of the sample fluid with a specified volume of the dilution fluid, the sample fluid can, in a first step, first be transported by means of the first pump 12 via the first fluid flow path into the dosing chamber 22, and the specified volume can be measured using the detector signals of at least one of the detectors 29, 30, 31. For this purpose, the electronic measuring and control system 15 stops the fluid transport via the second, the third, and the fourth fluid flow paths by operating the second pump 13 in the second operating mode blocking the fluid transport, by closing the valve 26 so that it blocks the fluid transport through the fluid line 26, and by closing the valve 39 so that a fluid transport through the fluid line 18 is also blocked. In the process, the valve 24 is open, so that the dosing chamber 22 is connected via the line 23 to the atmosphere. The valve 37 and the valves of the valve unit 25 are also closed. If the fill level in the dosing chamber 22 reaches that of the detectors 29, 30, 31, the position of which corresponds to the fill level used for the dosing in the dosing chamber 22, the first pump 12 is stopped or put into its second operating mode. At the same time, a fluid transport via the first fluid flow path is thereby blocked. The valves of the central valve unit 25 are at the same time set such that they block a fluid transport through the lines that connect the tanks 3, 4, 5, 6 and 41 to the dosing chamber 22. The valves of the valve unit 25 remain in this position in all method steps described below, in which no fluid is taken from one of the tanks 3, 4, 5, 6 or 41.

The volume measured in the described manner of the sample fluid is transported in a second step from the dosing chamber 22 via a fourth fluid flow path into the mixing tank 11. In doing so, the valve 39 is open, while the valves 24, 27 and 37 are closed so that a fluid transport via the discharge line 28 and along the third fluid flow path is blocked. The pumps 12 and 13 remain in their second operating state and thus block a fluid transport along the first and the second fluid flow paths so that only the fourth fluid flow path is unblocked.

In a third step, dilution fluid is transported via the supply line 21 and the second fluid flow path into the dosing chamber 22 by means of the second pump 13, in order to measure a specified volume of the dilution fluid. The third step is carried out using the second pump 13 in a way analogous to that described herein for the measuring of a specified volume of the sample fluid using the first pump 12.

In a fourth step, the measured volume of the dilution fluid is added from the dosing chamber 22 via the fourth fluid flow path into the mixing tank 11 to the sample fluid already present there. The fourth step is also carried out analogously to the previously described transport of the sample fluid from the dosing chamber 22 via the fourth fluid flow path into the mixing tank 11.

The first and second steps and/or the third and fourth steps in the dosing of the sample fluid and/or the dilution fluid may be repeated once or several times, in order to dose greater volumes of the sample fluid and/or the dilution fluid into the mixing tank 11.

A gas such as air may be supplied to the mixing tank 11 in order to better mix the sample fluid and the dilution fluid in the mixing tank 11. For this purpose, air is first taken in via the gas supply line 23 by means of the third pump 14. When doing so, the valve 24 is open, the valves 27, 37, 39 are closed, and the pumps 12 and 13 are in their second operating state. Afterwards, the air taken in by the third pump 14 is supplied to the mixing tank 11 via the dosing chamber 22 and the fourth fluid transport path. When doing so, the valve 39 is open, the valves 24, 27, 37 are closed, and the pumps 12 and 13 are in their second operating state. The taking in of air and the transporting of the air into the mixing tank 11 can also be repeated several times when needed, in order to achieve an optimal mixing and possibly a suspension of the solid contents in the mixture contained in the mixing tank 11. If the sample fluid contains solid contents, the mixing with air may be performed shortly before the taking of a sample from the mixing tank 11 for a measurement.

A specified volume of the mixture can be taken from the mixing tank 11 by means of the dosing device 9 and transported via the third fluid flow path as sample into the measuring cell 7. For this purpose, the first and the second pumps 12 and 13 remain in the second operating state, i.e., they are not involved in the fluid transport, and block the fluid lines 16 and 20 or the first and second fluid flow paths. The valve 39 is opened, and, with closed valves 24, 27, and 37, the fluid is transported via the third fluid flow path into the dosing chamber 22. By means of the third pump 14 and the detectors 29 to 31, a specified volume of the mixtures is measured using the signals of the detectors 29, 30, 31. The measured volume is then transported further into the measuring cell 7 by means of the third pump 14, wherein the valves 27 and 35 are open, the valves 24, 37, and 39 are closed, and the pumps 12 and 13 continue to block a fluid transport through the first and second fluid flow paths.

In a further step, one or more reagents are then dosed by means of the dosing device 9 from the tanks 3, 4, 5, 6 or 41 into the measuring cell for sampling, depending upon the type of the parameter to be determined. This is carried out analogously to the dosing of the sample into the measuring cell 7, wherein, instead of the valve 39, the respective valve of the valve unit 25, unblocking the transport of the respective reagent into the dosing device 9, is opened, in order to transport the reagent into the dosing chamber and to measure a certain volume of the reagent by means of the dosing device 9. Using the third pump 14, all reagents needed for the determination of the parameter to be determined are, one after the other, transported into the measuring cell 7 and form a reaction mixture there. One or more substances (i.e., analytes) present in the sample and influencing the value of the parameter to be determined undergo a chemical reaction with the reagents, which reaction leads to either a consumption or the formation of a colored substance, for example. The measuring radiation of the sensing element 8 is selected such that it comprises at least one wavelength, which is absorbed by the substance. The absorption of the measuring radiation by the substance influences the intensity detected by the detector 33. The signal generated by the detector and output to the electronic measuring and control system is thus, according to the Beer-Lambert law, a measure of the concentration of the substance, which in turn is a measure of the analyte concentration in the sample. Based upon a calibration function or calibration table stored in the electronic measuring and control system 15, the electronic measuring and control system 15 can determine a measured value of the parameter to be determined from the signal of the detector. This measured value is output via a user interface or via an interface to a higher-level unit.

After determining the measured value, the spent reaction mixture can be discharged from the measuring cell 7 by first conducting the reaction mixture via the third fluid flow path into the dosing chamber 22 by means of the third pump 14, wherein the valves 27 and 35 are open, the valves 24, 37, 39 are closed, and the pumps 12 and 13 remain in the second operating mode, so that only the third fluid flow path is unblocked for the fluid transport. Subsequently, the spent reaction mixture is discharged via the discharge line 28 from the dosing chamber 22, wherein the valves 24, 27, and 39 are closed and the valve 37 is open, and the pumps 12 and 13 remain in their second operating mode. When needed, these steps can be repeated until the measuring cell 7 is completely emptied.

Analogously, the mixing tank 11 can be emptied either already before the supplying of the reagents into the measuring cell 7, during the carrying out of the chemical reaction, and/or during the measurement in the measuring cell 7, or subsequently thereto. Additional steps, such as the pre-rinsing or post-rinsing of lines, dosing chamber 22, mixing tank 11, or measuring cell 7 with sample fluid, dilution fluid, reagents, standard and/or cleaning solution, can also be inserted into the sequence.

All method steps described here are carried out in an automated manner in the example described here by the electronic measuring and control system 15, which controls for this purpose the valves and pumps, as well as the sensing element 8 of the analyzer 1, in accordance with a specified sequence program using the signals of the detectors 29, 30, 31 and possibly of the leak detector 38.

In the case where the sample fluid does not have to be diluted prior to supplying it into the measuring cell 7, the analyzer 1 shown in FIG. 1 can transport the sample fluid directly via the first fluid flow path into the dosing chamber 22 by means of the first pump 12. Subsequently, the volume, measured in this way, of the diluted sample fluid can be conducted as sample via the third fluid flow path into the measuring cell 7 by means of the third pump 14. The analyzer 1 thus allows for the determination of the parameter over a broad concentration range, since measurements can be carried out both with the diluted sample fluid and with a sample of the diluted sample fluid, wherein the dilution ratio can be set flexibly.

A plurality of modifications of the analyzer in accordance with the example described here is conceivable. For example, the mixing tank can be dispensed with, and the mixing of the sample fluid with the dilution medium can be carried out directly in the measuring cell. A plurality of alternative embodiments of the first, second, third, and fourth fluid flow paths through fluid lines and valve units is also conceivable for the person skilled in the art, and implementable.

The exemplary embodiment described with reference to FIG. 1 needs only very few fluid lines, valves, pumps, and other functional modules. It is particularly advantageous that the dosing device 9, which is used to dose the sample and the reagents into the measuring cell, is also used to set the dilution ratio between the sample fluid and the dilution fluid.

The invention claimed is:

1. An automatic analyzer for determining a parameter of a sample fluid, the automatic analyzer comprising:
    a dosing device including at least one dosing chamber;
    a first fluid flow path fluidically connecting a sample receiving vessel to the dosing chamber;
    a first pump integrated into the first fluid flow path for fluid transport along the first fluid flow path;
    a tank containing a dilution medium;
    a second fluid flow path fluidically connecting the tank containing the dilution medium to the dosing chamber;
    a second pump integrated into the second fluid flow path for fluid transport along the second flow path;
    a measuring cell enclosing a cavity in fluid communication with the dosing chamber via a third fluid flow path;
    a third pump connected to the dosing chamber; and
    an electronic measuring and control system in communication with the first, second and third pumps, the measuring and control system configured to control the first, second and third pumps,
    wherein each of the first, second and third fluid flow paths can selectively be blocked or unblocked using at least one valve, and wherein the measuring and control system is further configured to control the at least one valve to selectively block or unblock the first, second and third flow paths,
    wherein the dosing device has at least one detector including at least one light barrier, the at least one detector structured to generate an electrical signal when a predetermined fill level in the dosing chamber is exceeded or fallen below and to output the electrical signal to the measuring and control system, and
    wherein the measuring and control system is configured to receive and process the electrical signal output by the detector and to control the first, second or third pumps based upon the electrical signal output by the detector to dose a specified volume of fluid contained in the dosing chamber.

2. The automatic analyzer of claim 1, further comprising:
    a mixing tank in fluid communication with the dosing chamber via a fourth fluid flow path, wherein the fourth flow path can be selectively blocked or unblocked using a first valve controlled by the measuring and control system.

3. The automatic analyzer of claim 1, wherein the first fluid flow path includes a first fluid line having two ends, the first fluid line opening into the sample receiving vessel on one end and the other end fluidically connected to the dosing chamber.

4. The automatic analyzer of claim 1, further comprising a second fluid line having two ends, the second fluid line opening into the tank containing the dilution medium on one end and the other end fluidically connected to the dosing chamber such that the second fluid flow path runs through the second fluid line.

5. The automatic analyzer of claim 1, wherein the first pump is embodied to transport fluid along the first fluid flow path in a first operating mode and to block the first fluid flow path in a second operating mode, and wherein the second pump is embodied to transport fluid along the second fluid flow path in a first operating mode and to block the second fluid flow path in a second operating mode.

6. The automatic analyzer of claim 1, further comprising a third fluid line having two ends, the third fluid line opening into the measuring cell on one end and the other end fluidically connected to the dosing chamber such that the third fluid flow path runs through the third fluid line, wherein the third fluid line can be selectively blocked or unblocked using a second valve controlled by the measuring and control system.

7. The automatic analyzer of claim 2, further comprising a fourth fluid line having two ends, the fourth fluid line opening into the mixing tank on one end and the other end fluidically connected to the dosing chamber such that the fourth fluid flow path runs through the fourth fluid line, wherein the fourth fluid line can be selectively blocked or unblocked using the first valve controlled by the measuring and control system.

8. The automatic analyzer of claim 1, wherein the first and second pumps are peristaltic pumps and the third pump a piston pump, which includes a cylinder in communication with the dosing chamber and a movable piston disposed within the cylinder, the movable piston sealing the cylinder from the environment in a fluid-tight manner.

9. The automatic analyzer of claim 1, wherein the dosing chamber and/or the third pump communicate with a gas supply line via which the third pump can draw in a gas, or air from the environment, and transport the gas or air into the mixing tank or the measuring cell.

10. The automatic analyzer of claim 1, further comprising a first overflow line that opens into an upper region of the dosing chamber and/or a second overflow line that opens into an upper region of the mixing tank, and/or a third overflow line that opens into an upper region of the measuring cell.

11. The automatic analyzer of claim 10, further comprising a leak detector connected to the first, second and/or third overflow lines, the leak detector embodied to generate an electrical overflow signal when fluid escapes from the first, second and/or third overflow lines connected to the leak detector.

12. The automatic analyzer of claim 1, wherein the dosing chamber is fluidically connected via a third valve controlled by the measuring and control system, the third valve unit including a plurality of valves in communication with a plurality of tanks, the plurality of tanks containing different fluids, including one or more reagents, one or more calibration standards, one or more cleaning fluids, and/or fluids spent by the analyzer.

13. The automatic analyzer of claim 1, further comprising a sensing element disposed in or on the measuring cell to detect a measurand of a fluid or fluid mixture contained in the cavity of the measuring cell, the measurand correlated with a parameter of the fluid sample, the sensing element structured to generate an electrical measurement signal dependent upon the measurand and to output the measurement signal to the measuring and control system, wherein the measuring and control system is configured to process the measurement signal generated by the sensing element to determine a value of the parameter based upon the measurement signal.

14. The automatic analyzer of claim 1, further comprising a first fluid line, a second fluid line and a third fluid line, each embodied as a hose.

15. A method for operating an automatic analyzer, the method comprising:
   transporting a sample fluid from a sample receiving vessel into a dosing chamber of a dosing device of an analyzer using a first pump, wherein the analyzer includes:
      the dosing device including the dosing chamber,
      a first fluid flow path fluidically connecting a sample receiving vessel to the dosing chamber,
      the first pump integrated into the first fluid flow path for fluid transport along the first fluid flow path,
      a tank containing a dilution medium,
      a second fluid flow path fluidically connecting the tank containing the dilution medium to the dosing chamber,
      a second pump integrated into the second fluid flow path for fluid transport along the second flow path,
      a measuring cell enclosing a cavity in fluid communication with the dosing chamber via a third fluid flow path,
      a third pump connected to the dosing chamber, and
      an electronic measuring and control system in communication with the first, second and third pumps, the measuring and control system configured to control the first, second and third pumps, wherein each of the first, second and third fluid flow paths can selectively be blocked or unblocked using at least one valve, wherein the measuring and control system is further configured to control the at least one valve to selectively block or unblock the first, second and third flow paths,
   wherein the dosing device has at least one detector including at least one light barrier, the at least one detector structured to generate an electrical signal when a predetermined fill level in the dosing chamber is exceeded or fallen below and to output the electrical signal to the measuring and control system, and
   wherein the measuring and control system is configured to receive and process the electrical signal output by the detector and to control the first, second or third pumps based upon the electrical signal output by the detector to dose a specified volume of fluid contained in the dosing chamber;
   dosing a specified volume of the sample fluid using the dosing device;
   transporting dilution medium from the tank containing the dilution medium into the dosing chamber using the second pump;
   dosing a specified volume of the dilution medium using the dosing device; and
   mixing the specified volume of the sample fluid with the specified volume of the dilution medium.

16. The method of claim 15, wherein the mixing of the specified volume of the sample fluid with the specified volume of the dilution medium comprises:
   transporting the specified volume of the sample fluid into a mixing tank using the third pump communicating with the dosing chamber; and
   transporting the specified volume of the dilution medium into the mixing tank using a third pump.

17. The method of claim 16, further comprising:
   transporting a gas or gas mixture into and/or through a fluid mixture formed in the mixing tank by mixing the specified volume of the sample fluid with the specified volume of the dilution medium;
   transporting at least a part of the fluid mixture into the dosing chamber using the third pump;
   dosing a specified volume of the fluid mixture using the dosing device;
   transporting the specified volume of the fluid mixture into a measuring cell;
   transporting at least one reagent into the measuring cell;
   detecting a measured value of a measurand of the fluid mixture in the measuring cell and mixed with the reagent, the measurand being correlated with a parameter to be determined of the sample fluid; and
   determining a value of the parameter based upon the detected measured value.

18. The method of claim 15, wherein the method is performed in an automated manner using the measuring and control system.

* * * * *